(12) United States Patent
Beitone et al.

(10) Patent No.: US 8,545,817 B2
(45) Date of Patent: Oct. 1, 2013

(54) COSMETIC COMPOSITION COMPRISING AT LEAST ONE POLYSACCHARIDE OF λ-CARRAGEENAN TYPE IN AEROSOL FORM, METHOD FOR THE COSMETIC TREATMENT OF KERATINOUS FIBERS, AND PRODUCT COMPRISING THE COMPOSITION

(75) Inventors: Régis Beitone, Paris Cedex (FR); Ludivine Laurent, Courbevoie (FR)

(73) Assignee: L'Oreal, Paris (FR)

( * ) Notice: Subject to any disclaimer, the term of this patent is extended or adjusted under 35 U.S.C. 154(b) by 668 days.

(21) Appl. No.: 11/882,777

(22) Filed: Aug. 6, 2007

(65) Prior Publication Data

US 2008/0031829 A1 Feb. 7, 2008

(30) Foreign Application Priority Data

Aug. 4, 2006 (FR) ..................................... 06 07156

(51) Int. Cl.
*A61K 8/02* (2006.01)
*A61K 9/12* (2006.01)
*A61K 9/14* (2006.01)

(52) U.S. Cl.
USPC .................. 424/47; 424/45; 424/46; 424/401

(58) Field of Classification Search
USPC ........................... 424/45, 46, 401, DIG. 1, 47
See application file for complete search history.

(56) References Cited

U.S. PATENT DOCUMENTS

| | | | |
|---|---|---|---|
| 2,047,398 A | 7/1936 | Voss et al. | |
| 2,102,113 A | 12/1937 | Djordjevitch | |
| 2,723,248 A | 11/1955 | Wright | |
| 3,589,578 A | 6/1971 | Kamphausen | |
| 3,836,537 A | 9/1974 | Boerwinkle et al. | |
| 3,966,403 A | 6/1976 | Papantoniou et al. | |
| 3,966,404 A | 6/1976 | Papantoniou et al. | |
| 3,990,459 A | 11/1976 | Papantoniou et al. | |
| 4,031,307 A | 6/1977 | DeMartino et al. | |
| 4,128,631 A | 12/1978 | Lyndmark et al. | |
| 4,131,576 A | 12/1978 | Lovino et al. | |
| 4,137,180 A | 1/1979 | Naik et al. | |
| 4,137,208 A | 1/1979 | Elliott et al. | |
| 4,185,087 A | 1/1980 | Morlino | |
| 4,282,203 A | 8/1981 | Jacquet et al. | |
| 4,289,752 A | 9/1981 | Mahieu et al. | |
| 4,874,554 A | 10/1989 | Lange et al. | |
| 5,070,171 A | 12/1991 | O'Lenick, Jr. | |
| 5,091,493 A | 2/1992 | O'Lenick, Jr. et al. | |
| 5,093,452 A | 3/1992 | O'Lenick, Jr. | |
| 5,149,765 A | 9/1992 | O'Lenick, Jr. | |
| 5,538,717 A | 7/1996 | La Poterie | |
| 6,024,948 A * | 2/2000 | Samain et al. ............. | 424/70.16 |
| 6,106,813 A | 8/2000 | Mondet et al. | |
| 6,166,093 A | 12/2000 | Mougin et al. | |
| 6,228,378 B1 * | 5/2001 | Takanabe et al. ............. | 424/401 |
| 6,372,876 B1 | 4/2002 | Kim et al. | |
| 6,395,265 B1 | 5/2002 | Mougin et al. | |
| 6,623,727 B2 | 9/2003 | Birkel et al. | |
| 2002/0076387 A1 | 6/2002 | Birkel et al. | |
| 2003/0147822 A1 * | 8/2003 | Doi et al. ..................... | 424/70.1 |
| 2004/0170575 A1 * | 9/2004 | Belli et al. ..................... | 424/47 |
| 2006/0134049 A1 | 6/2006 | Keenan et al. | |

FOREIGN PATENT DOCUMENTS

| | | |
|---|---|---|
| EP | 0 080 978 | 6/1983 |
| EP | 0 445 659 | 9/1991 |
| EP | 0 492 657 | 7/1992 |
| EP | 0 530 974 | 3/1993 |
| EP | 0 619 111 | 10/1994 |
| EP | 0 656 021 | 6/1995 |
| EP | 0 664 113 | 7/1995 |
| EP | 0 920 851 | 6/1999 |
| FR | 1584110 | 12/1969 |
| FR | 2357241 | 2/1978 |
| GB | 839805 | 6/1960 |
| GB | 922457 | 4/1963 |
| GB | 1021400 | 3/1966 |
| GB | 1169862 | 11/1968 |
| GB | 1231452 | 5/1971 |
| GB | 1331819 | 9/1973 |
| GB | 2000026 | 1/1974 |
| GB | 1408388 | 10/1975 |
| GB | 1572626 | 7/1980 |
| JP | 62-289508 | 12/1987 |
| JP | 62-294606 | 12/1987 |
| JP | 2-157214 | 6/1990 |
| JP | 5-178718 | 7/1993 |
| JP | 10-25227 | 1/1998 |
| JP | 2002-87993 | 3/2002 |
| JP | 2003-212731 | 7/2003 |
| WO | WO 94/03510 | 2/1994 |

OTHER PUBLICATIONS

English language Abstract of JP 62-289508, dated Dec. 16, 1987.
English language Abstract of JP 62-294606, dated Dec. 22, 1987.
English language Abstract of JP 2-157214, dated Jun. 18, 1990.
English language Abstract of JP 5-178718, dated Jul. 20, 1993.
English language Abstract of JP 10-25227, dated Jan. 27, 1998.
English language Abstract of JP 2002-87993, dated Mar. 27, 2002.
English language Abstract of JP 2003-212731, dated Jul. 30, 2003.
Porter, M.R., "Handbook of Surfactants," Blackie & Son (Glasgow and London, pp. 116-178, 1991).
English Language abstract of EP 0 080 976 from esp@cenet, Feb. 19, 2008.
English Language Machine Translation of FR 1,584,110 from esp@cenet, Feb. 21, 2008.
English Language Machine Translation of FR 2,357,241 from esp@cenet, Mar. 4, 2008.
International Search Report for FR 0607156, dated Mar. 30, 2007 (corresponding to the present application).

\* cited by examiner

*Primary Examiner* — James H. Alstrum-Acevedo
(74) *Attorney, Agent, or Firm* — O'Brien Jones PLLC

(57) ABSTRACT

Disclosed herein is a cosmetic composition for the treatment of keratinous fibers, for example, human keratinous fibers, such as the hair, in the form of an aerosol comprising at least one polysaccharide of lambda-carrageenan type and carbon dioxide as propellant. Also disclosed herein is a cosmetic treatment method for keratinous fibers comprising applying such a composition to the keratinous fibers.

16 Claims, No Drawings

COSMETIC COMPOSITION COMPRISING AT LEAST ONE POLYSACCHARIDE OF λ-CARRAGEENAN TYPE IN AEROSOL FORM, METHOD FOR THE COSMETIC TREATMENT OF KERATINOUS FIBERS, AND PRODUCT COMPRISING THE COMPOSITION

This application claims benefit of priority under 35 U.S.C. §119 to French Patent Application No. FR 06/07156, filed Aug. 4, 2006, the contents of which are incorporated herein by reference.

Disclosed herein is a cosmetic composition for the treatment of keratinous fibers, for example, human keratinous fibers, such as the hair, in the form of an aerosol composition comprising at least one polysaccharide of lambda-carrageenan type and carbon dioxide as propellant gas. Also disclosed is a cosmetic treatment method for fixing keratinous fibers comprising applying a cosmetic composition of the present disclosure to the fibers.

Many common cosmetic compositions for shaping and/or retaining the hairstyle on the cosmetics market include compositions to be sprayed or to be dispersed in mousse form comprising a solution, generally an alcoholic or aqueous/alcoholic solution, and at least one component, generally polymer resins, the role of which is either to form joins between the hairs or sheath the latter. These components are generally referred to as fixing components and are often present as a mixture with various cosmetic adjuvants. This solution is generally packaged either in an appropriate aerosol container pressurized using a propellant or in a pump-action spray.

Numerous aerosol systems intended to fix or to sheath the hair are known, these systems comprising, on the one hand, a liquid phase (or dispensable) and, on the other hand, a propellant. The role of the latter is to provide a pressure which makes it possible to disperse the liquid phase in the form of a spray or of a mousse.

Recently, carrageenans have been used as fixing polymers in styling gels or in aerosols. For example, European Patent No. 1 199 064 discloses the use of a carrageenan or a mixture of a carrageenan and a specific additive in order to obtain a solid and stable gel for hair treatment.

Carrageenans are polysaccharides which form the cell walls of various red algae (Rhodophyceae) belonging to the families of the Gigartinaceae, Hypneaceae, Furcellariaceae, and Polyideaceae. They comprise long galactan chains which are anionic polyelectrolytes. Their molecular weights can be greater than $10^6$. These linear polymers, formed by disaccharide units, are composed of two D-galactopyranose units alternately bonded via α- and β-bonds. These are highly sulphated (20-50%) polysaccharides and the α-D-galactopyranosyl residues can be in the 3',6'-anhydro form.

The carrageenans were initially subdivided into two families according to their solubility in potassium chloride (KCl). The fractions soluble in KCl were designated by the prefixes "kappa", while the terms "lambda" were reserved for those which are insoluble. Later, the classifications were based on the number of sulphate groups, the position of sulphate groups and the presence of 3',6'-anhydro bridge on the β-D-galactopyranosyl residues. This resulted in four main families: κ, λ, β, and ω.

The various types of carrageenans do not exist in the pure state but in the form of hybrids. Thus, in the natural state, the κ- and τ-carrageenans exist in a kappa-iota hybrid form but one of the two structures may predominate over the other. The κ-τ hybrid state of a structure can be elucidated using specific enzymes which make it possible to enrich or reduce the content of one of the two forms. The carrageenans can coexist with their precursors. The carrageenans belonging to different families can coexist in a hybrid structure, for example: carrageenan from *Euchema gelatinae*, a hybrid of β-carrageenan, major component, and of κ- and γ-carrageenans.

Hair compositions in aerosol form comprising a polysaccharide of λ-carrageenan type make it possible to obtain hair mousses with very good styling and care properties. However, the use of conventional propellant gases, of hydrocarbon and mixtures of hydrocarbons type, does not make it possible to obtain satisfactory mousses.

Accordingly, there is a need in the art to find cosmetic compositions, such as compositions for hair styling, which make it possible to improve the quality of the mousse and which may make it possible to obtain gels with better textures which are less likely to break down, which are softer, and which are easier to apply.

The inventors have discovered, surprisingly, that by using carbon dioxide as propellant gas for compositions based on at least one polysaccharide of λ-carrageenan type, it is possible to obtain a styling mousse with a novel texture: creamy mousse which is easy to spread and which is not expanded to any great extent.

Furthermore, the use of carbon dioxide as propellant gas in combination with a polysaccharide of λ-carrageenan type makes it possible to obtain an entirely natural mousse.

Thus, disclosed herein is a cosmetic composition for the treatment of keratinous fibers, for example, human keratinous fibers, such as the hair, comprising, in a cosmetically acceptable medium:

at least one polysaccharide of lambda-carrageenan type, and carbon dioxide as propellant gas.

Also disclosed herein is a cosmetic treatment method for fixing and/or caring for keratinous fibers comprising applying to the fibers at least one cosmetic composition according to the present disclosure.

Other subject-matters, characteristics, aspects and benefits of the present disclosure will become more apparent upon reading the description and examples which follow.

As used herein, the word "styling" is understood to mean fixing and/or retaining the form of the hairstyle.

The composition according to the present disclosure comprises at least one polysaccharide of lambda-carrageenan type.

In at least one embodiment, the polysaccharide of lambda-carrageenan type used according to the present disclosure is not chemically modified.

According to another embodiment, the molecular weight (MW) of the polysaccharide ranges from 100,000 to 1,000,000. In yet another embodiment, the molecular weight ranges from 250,000 to 800,000.

Non-limiting examples of polysaccharides of lambda-carrageenan type which can be used in accordance with the present disclosure include Satiagum UTC 10 from Degussa and Welgeenan ED 1039 from Eurogum.

The polysaccharide of lambda-carrageenan type may be present in the composition in an amount ranging from 0.1 to 30%, for example, from 0.2 to 20%, or from 0.5 to 15% by weight, with respect to the total weight of the aerosol composition.

The dispenser generally comprises a dispensing valve controlled by a dispensing head, itself comprising a nozzle via which the aerosol composition is vaporized.

According to one embodiment of the present disclosure, the aerosol device according to the present disclosure is appropriate for obtaining a dry matter throughput of greater than or equal to 20 mg/s, for example, ranging from 20 mg/s to 60 mg/s.

According to the present disclosure, the dry matter throughput (DMT) corresponds to the amount, on a dry basis, which exits from the aerosol device per unit of time. This dry matter throughput is expressed in mg/s and is calculated by multiplying the concentration of dry matter in the aerosol composition (CDM) by the throughput of the aerosol composition at the outlet of the nozzle (ACT):

DMT=CDM×ACT.

The concentration of dry matter in the aerosol composition (CDM) corresponds to the amount of dry matter with respect to 100 g of the aerosol composition (dispensable+propellant). The concentration of dry matter is expressed as a percentage and is measured after spraying by evaporation of the volatile components from the spray residue at 105° C. for 1 hour and 30 minutes.

The aerosol composition throughput (ACT) corresponds to the amount of aerosol composition (dispensable+propellant) exiting from the aerosol device per unit of time. It is expressed in mg/s and is measured by the difference between the weight of the aerosol before (M0) and after (M1) vaporizing for 10 seconds:

ACT=(M0−M1)/10.

According to one embodiment, the concentration of dry matter (CDM) may range from 2.5 to 15% by weight, with respect to the total weight of the aerosol composition (dispensable+propellant), for example, from 3.5 to 10% by weight.

The aerosol composition throughput (ACT) will then be appropriate for obtaining a dry matter throughput (DMT) as defined above. In at least one embodiment, the ACT may range from 500 to 800 mg/s, for instance, 600 mg/s.

The phase of the aerosol composition is, according to one embodiment, a long phase, that is to say that the dispensable/propellant ratio by weight is greater than 1, such as ranging from 1.2 to 3.

In at least one embodiment, the propellant is present in the aerosol composition in an amount ranging from 2 to 70%, for instance, from 3 to 50%, by weight, with respect to the total weight of the combined compositions present in the aerosol device.

A person skilled in the art will know how to select the appropriate dispenser according to the aerosol composition (dispensable+propellant) in order to obtain the desired dry matter throughput characteristics.

The characteristics defined above (CDM and phase) can be obtained by selecting the appropriate dispensing means and/or by varying the formulation.

The valves appropriate for the compositions may include, by way of non-limiting example, straight-line valves with a spray nozzle having a diameter ranging from 0.35 to 0.60 mm, for instance, from 0.40 to 0.50 mm, optionally without internal restriction and/or an additional gas connection. Examples of such valves include, but are not limited to, the valves sold under the name Coster T104 RA36/0/4 by Coster and the Precision Experimental 15130 valve, comprising a spray nozzle and a valve body with a diameter of 0.46 mm without an additional gas connection, from Precision.

The diffusers appropriate for the compositions above include, but are not limited to, the push-buttons sold under the name Precision 216903-50AD29 by Precision.

The composition may optionally further comprise at least one optional component.

The cosmetic composition according to the present disclosure may further comprise at least one silicone.

As used herein, the term "silicone" means, in conformity with what is generally accepted, any organosilicon polymer or oligomer with a linear or cyclic, branched or crosslinked structure, of variable molecular weight, obtained by polymerization and/or by polycondensation of suitably functionalized silanes and essentially composed of a repetition of main units in which the silicon atoms are connected to one another via oxygen atoms (siloxane —Si—O—Si— bond), optionally substituted hydrocarbon radicals being directly connected via a carbon atom to the said silicon atoms. The most common hydrocarbon radicals are alkyl radicals, such as $C_1$-$C_{10}$ alkyl radicals, for instance, methyl radicals, fluoroalkyl radicals, the alkyl part of which is a $C_1$-$C_{10}$ alkyl radical, and aryl radicals such as the phenyl radical.

In at least one embodiment, the silicone is an oxyalkylene silicone.

As used herein, the term "oxyalkylene silicone" is understood to mean any silicone comprising at least one oxyalkylene group of $(-C_xH_{2x}O-)_a$ type in which x can range from 2 to 6 and a is greater than or equal to 2.

The oxyalkylene silicones which can be used in the cosmetic composition may be chosen from compounds of formulae (VI), (VII), (VIII), and (IX):

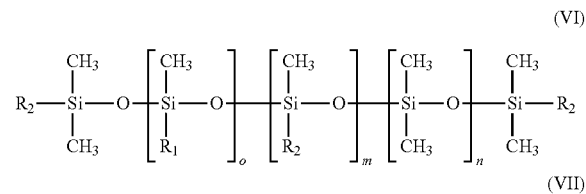

(VI)

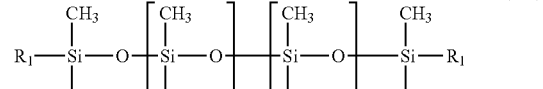

(VII)

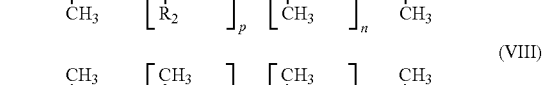

(VIII)

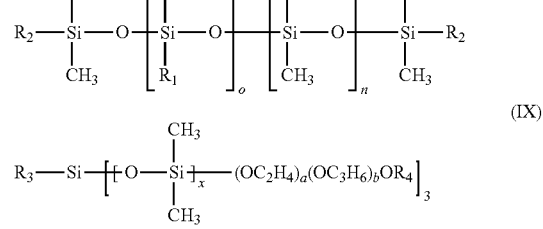

(IX)

wherein:

$R_1$, which may be identical or different, are chosen from linear and branched $C_1$-$C_{30}$ alkyl radicals and phenyl radicals, $R_2$, which may be identical or different, are chosen from —$C_cH_{2c}$—O—$(C_2H_4O)_a(C_3H_6O)_b$—$R_5$ radicals and —$C_cH_{2c}$—O—$(C_4H_8O)_a$—$R_5$ radicals, $R_3$ and $R_4$, which may be identical or different, are chosen from linear and branched $C_1$ to $C_{12}$ alkyl radicals, such as the methyl radical, $R_5$, which may be identical or different, are chosen from hydrogen, linear and branched alkyl radicals comprising from 1 to 12 carbon atoms, linear and branched alkoxy radicals comprising from 1 to 6 carbon atoms, linear and branched acyl radicals comprising from 2 to 30 carbon atoms, hydroxyl radicals, —$SO_3M$ radicals, $C_1$-$C_6$ aminoalkoxy radicals optionally substituted on the amine, $C_2$-$C_6$ aminoacyl radicals optionally substituted on the amine, —NHCH$_2$CH$_2$COOM radicals, —N(CH$_2$CH$_2$COOM)$_2$ radicals, aminoalkyl radicals optionally substituted on the amine and on the alkyl chain, $C_2$-$C_{30}$ carboxyacyl radicals, groups optionally substituted by one or two substituted aminoalkyl radicals, —CO(CH$_2$)$_d$COOM groups, —COCHR$_7$(CH$_2$)$_d$COOM groups, —NHCO(CH$_2$)$_d$OH groups, —NH$_3$Y groups, and phosphate groups, M, which may be identical or different, are chosen from hydrogen, Na, K, L$_1$, NH$_4$, and organic amines, R$_7$ is chosen from hydrogen and SO$_3$M radicals, d ranges from 1 to 10, m ranges from 0 to 20, n ranges from 0 to 500, o ranges from 0 to 20, p ranges from 1 to 50, a ranges from 0 to 50, b ranges from 0 to 50, a+b is greater than or equal to 2, c ranges from 0 to 4, x ranges from 1 to 100, Y$^-$ is chosen from monovalent inorganic and organic anions, such as halides (e.g., chloride and bromide), sulphates, and carboxylates (e.g., acetate, lactate, and citrate), with the proviso that, when the silicone is of formula (VII) and when R$_5$ is hydrogen, then n is greater than 12.

Such silicones are, for example, sold by Goldschmidt under the tradenames Abil WE 09, Abil EM 90, Abil B8852, Abil B8851, Abil B 8843, and Abil B8842; by Dow Corning under the names Fluid DC 190, DC 3225 C, Q2-5220, Q2-5354, and Q2-5200; by Rhodia Chimie under the names Silbione Oil 70646 and Rhodorsil Oil 10634; by General Electric under the names SF1066 and SF1188; by SWS Silicones under the name Silicone Copolymer F 754; by Amerchol under the name Silsoft Beauty Aid SL; by Shin-Etsu under the name KF 351; by Wacker under the name Belsil DMC 6038; by Siltech under the names Silwax WD-C, Silwax WD-B, Silwax WD-IS, Silwax WSL, Silwax DCA 100, and Siltech Amine 65; by Fanning Corporation under the names Fancorsil SLA and Fancorsil LIM1, and by Phoenix under the name Pecosil.

These silicones are described, for example, in U.S. Pat. Nos. 5,070,171, 5,149,765, 5,093,452, and 5,091,493.

In one embodiment, the at least one silicone may be chosen from polyoxyalkylene silicones of formulae (VII) and (VIII). According to another embodiment, in formulae (VII) and (VIII), at least one of the following conditions exists:

c is equal to 2 or 3,

R$_1$ is a methyl radical,

R$_5$ is chosen from methyl radicals, C$_{12}$-C$_{22}$ acyl radicals, and CO(CH$_2$)$_d$COOM radicals, a ranges from 2 to 25, for example, from 2 to 15, b is equal to 0, n ranges from 0 to 100, and p ranges from 1 to 20.

The polyoxyalkylene silicones may also be chosen from the silicones of formula (X):

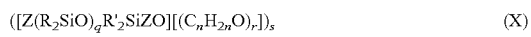

(X)

wherein:

R$_2$ and R'$_2$, which may be identical or different, are chosen from monovalent C$_1$-C$_{30}$ hydrocarbon radicals, n is an integer ranging from 2 to 4, q is a number greater than or equal to 4, for example, ranging from 4 to 200, or from 4 to 100, r is a number greater than or equal to 4, for instance, ranging from 4 to 200, or from 5 to 100, s is a number greater than or equal to 4, for example, ranging from 4 to 1000, or from 5 to 300, Z is a divalent organic group which is bonded to the adjacent silicon atom via a carbon-silicon bond and to the polyoxyalkylene (C$_n$H$_{2n}$O) block via an oxygen atom, the average molecular weight of each siloxane block ranges from 400 to 10,000, the average molecular weight of each polyoxyalkylene block ranges from 300 to 10,000, the siloxane blocks are present in the copolymer in an amount ranging from 10% to 95% by weight relative to the total weight of the block copolymer, it being possible for the number-average molecular weight of the block copolymer to range from 2,500 to 1,000,000, for instance, from 3,000 to 200,000, or from 6,000 to 100,000.

In one embodiment, R$_2$ and R'$_2$ may be chosen from linear and branched alkyl radicals, for example, methyl, ethyl, propyl, butyl, pentyl, hexyl, octyl, decyl, and dodecyl radicals, aryl radicals, for example, phenyl and naphthyl radicals, aralkyl radicals, for example, benzyl and phenylethyl radicals, and alkylaryl radicals, for example, tolyl and xylyl radicals.

According to another embodiment, Z is chosen from —R"—, —R"—CO—, —R"—NHCO—, —R"'—NH—CO—NH—R"'—, and —R"—OCONH—R"'—NHCO— groups, wherein R" is chosen from linear and branched, divalent, C$_1$-C$_6$ alkylene groups, for example, linear and branched ethylene, propylene, and butylene, and R"' is chosen from divalent alkylene groups and divalent arylene groups, such as —C$_6$H$_4$—, —C$_6$H$_4$—C$_6$H$_4$—, —C$_6$H$_4$—CH$_2$—C$_6$H$_4$— and —C$_6$H$_4$—C(CH$_3$)$_2$C$_6$H$_4$—.

In yet another embodiment, Z is chosen from divalent alkylene radicals, such as —C$_3$H$_6$— radicals and C$_4$H$_8$ radicals, which may be linear or branched.

The preparation of the block copolymers is described, for example, in European Patent Application No. 0 492 657 A1, the teaching of which are incorporated herein by reference in its entirety.

Such products are sold, for example, under the name Silicone Fluid FZ-2172 by OSI.

The at least one silicone can be provided in a form chosen from aqueous solutions, that is to say dissolved, aqueous dispersions and microdispersions, and aqueous emulsions.

The at least one silicone which can be used in the cosmetic composition may be chosen from silicone gums.

The silicone gums which can be used in the cosmetic composition include, by way of non-limiting example, polydiorganosiloxanes having high weight-average molecular weights ranging from 200,000 to 1,000,000, used alone or as a mixture in a solvent. This solvent can be chosen, for instance, from volatile silicones, polydimethylsiloxane (PDMS) oils, polyphenylmethylsiloxane (PPMS) oils, isoparaffins, polyisobutylenes, methylene chloride, pentane, dodecane, tridecanes, and mixtures thereof.

Non-limiting examples of suitable silicone gums include:
polydimethylsiloxane,
polydimethylsiloxane/methylvinylsiloxane gums,
polydimethylsiloxane/diphenylmethylsiloxane,
polydimethylsiloxane/phenylmethylsiloxane, and
polydimethylsiloxane/diphenylsiloxane/methylvinylsiloxane.

Mixtures of silicone gums may also be used, for example:

- mixtures formed from a polydimethylsiloxane hydroxylated at the chain end (named dimethiconol according to the nomenclature of the CTFA dictionary) and from a cyclic polydimethylsiloxane (named cyclomethicone according to the nomenclature of the CTFA dictionary), such as the product Q2 1401 sold by Dow Corning;
- mixtures formed from a polydimethylsiloxane gum with a cyclic silicone, such as the product SF 1214 Silicone Fluid from General Electric; this product is an SF 30 gum corresponding to a dimethicone, having a molecular weight of 500,000, dissolved in the SF 1202 Silicone Fluid oil corresponding to decamethylcyclopentasiloxane;
- mixtures of two PDMSs with different viscosities, for example, mixtures of a PDMS gum and of a PDMS oil, such as the product SF 1236 from General Electric. The product SF 1236 is the mixture of an SE 30 gum defined above, having a viscosity of 20 m²/s, and of an SF 96 oil with a viscosity of $5.10^{-6}$ m²/s. This product may comprise 15% of SE 30 gum and 85% of an SF 96 oil.

The at least one silicone which can be used in the cosmetic composition may also be chosen from aminated silicones.

As used herein, the term "aminated silicone" is understood to mean any silicone comprising at least one group chosen from primary, secondary, and tertiary amine functional groups and quaternary ammonium groups.

The aminated silicones used in the cosmetic composition according to the present disclosure may be chosen from:

(a) compounds of formula (XI):

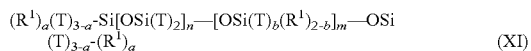
(XI)

wherein:

T is chosen from hydrogen, phenyl radicals, hydroxyl (—OH) radicals, $C_1$-$C_8$ alkyl radicals such as methyl radicals, and $C_1$-$C_8$ alkoxy radicals such as methoxy radicals, a is an integer ranging from 0 to 3, and in at least one embodiment, equal to 0, b is equal to 0 or 1, and in at least one embodiment, equal to 1, m and n are numbers such that the sum (n+m) ranges from 1 to 2,000, for example, from 50 to 150, wherein n is a number ranging from 0 to 1,999, such as from 49 to 149, and m is a number ranging from 1 to 2,000, such as from 1 to 10; and $R^1$ is a monovalent radical of formula —$C_qH_{2q}L$ wherein q is a number ranging from 2 to 8 and L is an aminated group, optionally quaternized, chosen from:

—N($R^2$)—CH$_2$—CH$_2$—N($R^2$)$_2$;

—N($R^2$)$_2$; —N$^+$($R^2$)$_3$Q$^-$;

—N$^+$($R^2$)(H)$_2$Q$^-$;

—N$^+$($R^2$)$_2$H Q$^-$; and

—N($R^2$)—CH$_2$—CH$_2$—N$^+$($R^2$)(H)$_2$Q$^-$;

wherein $R^2$ is chosen from hydrogen, phenyl radicals, benzyl radicals, and saturated monovalent hydrocarbon radicals, for example, $C_1$-$C_{20}$ alkyl radicals, and Q$^-$ is a halide ion, for example, fluoride, chloride, bromide, and iodide.

In at least one embodiment, the aminated silicones of formula (XI) may be chosen from compounds of formula (XII):

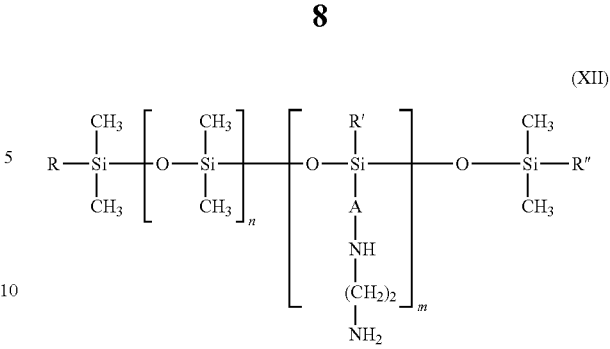

wherein R, R', and R", which may be identical or different, are chosen from $C_1$-$C_4$ alkyl radicals, such as CH$_3$, $C_1$-$C_4$ alkoxy radicals, such as methoxy, and OH radicals; A is chosen from linear and branched $C_3$-$C_8$, for instance, $C_3$-$C_6$, alkylene radicals; and m and n are integers depending on the molecular weight, the sum of which ranges from 1 to 2,000.

According to one embodiment, R, R', and R", which may be identical or different, are chosen from $C_1$-$C_4$ alkyl radicals and hydroxyl radicals, A is a $C_3$ alkylene radical and m and n are such that the weight-average molecular weight of the compound ranges from 5,000 to 500,000. The compounds of this type are named "amodimethicone" in the CTFA dictionary.

According to another embodiment, R, R', and R", which may be identical or different, are chosen from $C_1$-$C_4$ alkoxy radicals and hydroxyl radicals, at least one of the R or R" radicals is an alkoxy radical, and A is a $C_3$ alkylene radical. The hydroxyl/alkoxy molar ratio may range from 0.2/1 to 0.4/1, for example, equal to 0.3/1. Furthermore, m and n are such that the weight-average molecular weight of the compound ranges from 2,000 to $10^6$. In at least one embodiment, n ranges from 0 to 999 and m ranges from 1 and 1,000, the sum of n and m ranging from 1 to 1,000. A non-limiting example of this type of compound is the product Belsil®ADM 652 sold by Wacker.

According to yet another embodiment, R and R", which are different, are chosen from $C_1$-$C_4$ alkoxy radicals and hydroxyl radicals, at least one of the R and R" radicals is an alkoxy radical, R' is a methyl radical, and A is a $C_3$ alkylene radical. The hydroxyl/alkoxy molar ratio may range from 1/0.8 to 1/1.1, for example, equal to 1/0.95. Furthermore, m and n are such that the weight-average molecular weight of the compound ranges from 2,000 to 200,000. In at least one embodiment, n ranges from 0 to 999 and m ranges from 1 to 1,000, the sum of n and m ranging from 1 to 1,000. A non-limiting example of a product corresponding to this definition is the product Fluid WR® 1300 sold by Wacker.

According to a further embodiment, R and R" are hydroxyl radicals, R' is a methyl radical and A is chosen from $C_4$-$C_8$, for instance, $C_4$, alkylene radicals. Furthermore, m and n are such that the weight-average molecular weight of the compound ranges from 2,000 to $10^6$. In at least one embodiment, n ranges from 0 to 1,999 and m ranges from 1 to 2,000, the sum of n and m ranging from 1 to 2,000. A non-limiting example of a product of this type is that sold under the name DC28299 by Dow Corning.

The molecular weight of these silicones may be determined by gel permeation chromatography (ambient temperature, polystyrene standard; styragem µ columns; eluent THF; flow rate of 1 mm/m; 200 µl of a 0.5% by weight solution of silicone in THF are injected and the technique is carried out by refractometry and UV spectrometry).

A non-limiting example of a product corresponding to the definition of formula (XI) is the polymer named "trimethylsilylamodimethicone" in the CTFA dictionary, corresponding to formula (XIII):

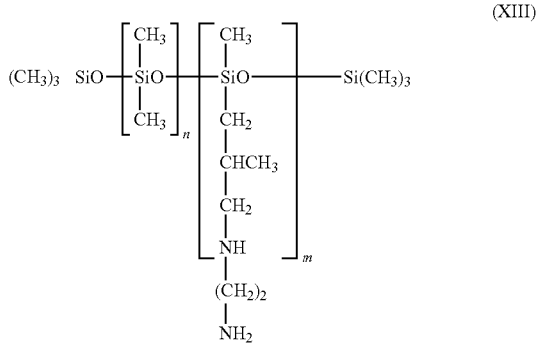

wherein n and m have the meanings given above in accordance with the formula (XI).

Such compounds are described, for example, in European Patent No. 0 095 238; and a compound of formula (XIII) is, for example, sold under the name Q2-8220 by OSI.

(b) compounds of formula (XIV):

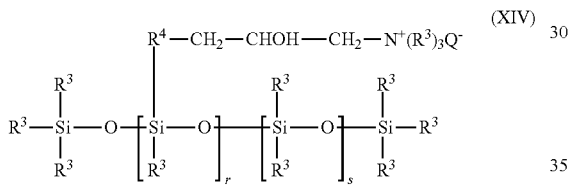

wherein:
R$^3$ is chosen from monovalent $C_1$-$C_{18}$ hydrocarbon radicals, such as $C_1$-$C_{18}$ alkyl and $C_2$-$C_{18}$ alkenyl radicals, for example methyl;
R$^4$ is chosen from divalent hydrocarbon radicals, such as $C_1$-$C_{18}$ alkylene radicals, and divalent $C_1$-$C_{18}$, for example, $C_1$-$C_8$, alkyleneoxy radicals;
Q$^-$ is a halide ion, for example, chloride;
r is a mean statistical value ranging from 2 to 20, such as from 2 to 8;
s is a mean statistical value ranging from 20 to 200, such as from 20 to 50.

Such compounds are described, for example, in U.S. Pat. No. 4,185,087.

A non-limiting example of a commercial product falling within this category is that sold by Union Carbide under the name "Ucar Silicone ALE 56".

(c) quaternary ammonium silicones of formula (XV):

wherein:
R$_7$, which may be identical or different, are chosen from monovalent hydrocarbon radicals comprising from 1 to 18 carbon atoms, such as $C_1$-$C_{18}$ alkyl radicals, $C_2$-$C_{18}$ alkenyl radicals, and rings comprising 5 or 6 carbon atoms, for example, methyl;
R$_6$ is chosen from divalent hydrocarbon radicals, for example, $C_1$-$C_{18}$ alkylene radicals, divalent $C_1$-$C_{18}$, for example, $C_1$-$C_8$, alkyleneoxy radicals connected to the Si via an SiC bond;
R$_8$, which may be identical or different, are chosen from hydrogen, monovalent hydrocarbon radicals comprising from 1 to 18 carbon atoms, such as $C_1$-$C_{18}$ alkyl radicals and $C_2$-$C_{18}$ alkenyl radicals, and —R$_6$—NHCOR$_7$ radicals;
X$^-$ is an anion chosen, for example, from halide ions, for instance, chloride, and organic acid anions (e.g., acetate, and the like); and
r is a mean statistical value ranging from 2 to 200, for example, from 5 to 100.

These silicones are described, for example, in European Patent Application No. 0 530 974.

(d) aminated silicones of formula (XVI):

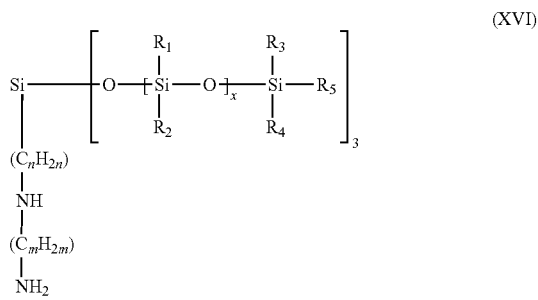

wherein:
R$_1$, R$_2$, R$_3$, and R$_4$, which may be identical or different, are chosen from $C_1$-$C_4$ alkyl radicals and phenyl groups,
R$_5$ is chosen from $C_1$-$C_4$ alkyl radicals and hydroxyl groups,
n is an integer ranging from 1 to 5,
m is an integer ranging from 1 to 5, and
x is chosen so that the amine number ranges from 0.01 to 1 meq/g.

According to one embodiment, the at least one silicone may be chosen from polysiloxanes comprising aminated groups, such as amodimethicones and trimethylsilylamodimethicones (CTFA, 4$^{th}$ edition, 1997), and silicones comprising quaternary ammonium groups.

According to this embodiment, when these compounds are employed, it may be beneficial to use them jointly with cationic and/or non-ionic surface-active agents.

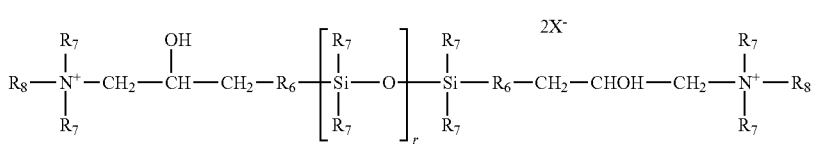

A non-limiting example of a commercial product falling within this embodiment is the product sold under the name "Cationic Emulsion DC 929" by Dow Corning, which comprises, in addition to the amodimethicone, a cationic surface-active agent comprising a mixture of products corresponding to the formula:

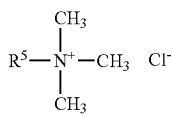

in which $R^5$ is chosen from $C_{14}$-$C_{22}$ alkenyl and/or alkyl radicals derived from tallow fatty acids, and known under the CTFA name "tallowtrimonium chloride," in combination with a non-ionic surface-active agent of formula: $C_9H_{19}$—$C_6H_4$—$(OC_2H_4)_{10}$—OH, known under the CTFA name "Nonoxynol 10".

Use may also be made, for example, of the product sold under the name "Cationic Emulsion DC 939" by Dow Corning, which comprises, in addition to the amodimethicone, a cationic surface-active agent which is trimethylcetylammonium chloride and a non-ionic surface-active agent of formula: $C_{13}H_{27}$—$(OC_2H_4)_{12}$—OH, known under the CTFA name "trideceth-12".

Another commercial product which can be used according to the present disclosure is the product sold under the name "Dow Corning Q2 7224" by Dow Corning, comprising, in combination, the trimethylsilylamodimethicone of formula (XVI) described above, a non-ionic surface-active agent of formula: $C_8H_{17}$—$C_6H_4$—$(OCH_2CH_2)_{40}$—OH, known under the CTFA name "octoxynol-40", a second non-ionic surface-active agent of formula: $C_{12}H_{25}$—$(OCH_2$—$CH_2)_6$—OH, known under the CTFA name "isolaureth-6", and propylene glycol.

The at least one silicone may be present in the composition in an amount ranging from 0.1 to 30%, for example, from 0.2 to 20%, or from 0.5 to 10% by weight, with respect to the total weight of the composition.

The cosmetic composition according to the present disclosure may further comprise at least one non-silicone fatty substance, such as vegetable, animal, mineral, and synthetic oils, fatty alcohols, fatty acids, and waxes.

The at least one fatty substance may be present in the composition in an amount ranging from 0.1 to 30%, for example, from 0.2 to 20%, or from 0.5 to 10% by weight, with respect to the total weight of the composition.

As used herein, the term "fatty alcohol" is understood to mean any pure, saturated or unsaturated, linear or branched, fatty alcohol comprising at least 8 carbon atoms. The fatty alcohol can be oxyalkylenated or glycerolated.

The fatty alcohol can exhibit the structure R—OH, wherein R is chosen from saturated and unsaturated, and linear and branched radicals comprising from 8 to 40 carbon atoms, for example, from 8 to 30 carbon atoms; and R is chosen from $C_{12}$-$C_{24}$ alkyl and $C_{12}$-$C_{24}$ alkenyl groups. R can optionally be substituted by at least one hydroxyl group.

Examples of fatty alcohols include, but are not limited to, lauryl, cetyl, dodecyl, decyl, stearyl, oleyl, behenyl, linoleyl, undecylenyl, palmitoleyl, arachidonyl, and erucyl alcohols and mixtures thereof.

The fatty alcohol may also be a mixture of fatty alcohols, which means that several types of fatty alcohols can coexist in a commercial product in the form of a mixture.

Non-limiting examples of mixtures of fatty alcohols include cetylstearyl and cetearyl alcohol.

According to one embodiment, the nonoxyalkylenated fatty alcohol is solid or pasty at a temperature of 25° C. As used herein, the term "fatty alcohol which is solid or pasty at 25° C." is understood to mean a fatty alcohol exhibiting a viscosity, measured with a rheometer with a shear rate of 1 $s^{-1}$, of greater than or equal to 1 Pa·s.

In another embodiment, the at least one fatty alcohol used in the cosmetic composition according to the present disclosure is chosen from cetyl alcohol and cetearyl alcohol.

As used herein, the term "fatty acids" is understood to mean any pure, saturated or unsaturated, linear or branched, carboxylic acid comprising at least 8 carbon atoms. Examples of fatty acid include, but are not limited to, lauric acid and oleic acid.

The cosmetic composition may further comprise at least one additional fixing polymer other than the fixing material of the present disclosure.

As used herein, the term "fixing polymer" is understood to mean any polymer which makes it possible to confer a form or to retain a given form or hairstyle.

The fixing polymers which can be used in the cosmetic composition according to the present disclosure may be chosen, by way of non-limiting example, from cationic, anionic, amphoteric, and non-ionic polymers, and mixtures thereof.

As used herein, the term "cationic polymer" is understood to mean any polymer comprising cationic groups and/or groups which can be ionized to give cationic groups.

The cationic fixing polymers which can be used in the cosmetic composition according to the present disclosure may be chosen, by way of non-limiting example, from polymers comprising primary, secondary, tertiary, and/or quaternary amine groups, which form part of the polymer chain or are directly connected to the latter, and having a number-average molecular weight ranging from 500 to 5,000,000, for example, from 1,000 to 3,000,000.

Examples of such cationic fixing polymers include, but are not limited to:

(1) homopolymers and copolymers of acrylic and methacrylic esters and amides, possessing amino functional groups, comprising at least one unit chosen from units of formulae (A)-(C):

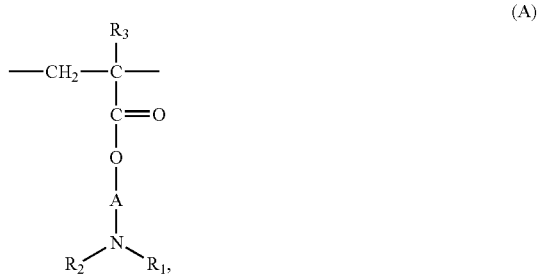

(A)

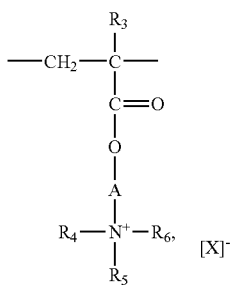
(B)

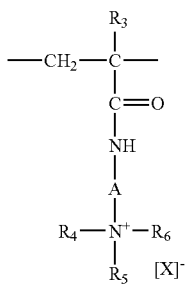
(C)

wherein:
R$_1$ and R$_2$, which may be identical or different, are chosen from hydrogen and alkyl groups comprising from 1 to 6 carbon atoms;
R$_3$ is chosen from hydrogen and CH$_3$;
A is chosen from linear and branched alkyl groups comprising from 1 to 6 carbon atoms and hydroxyalkyl groups comprising from 1 to 4 carbon atoms;
R$_4$, R$_5$, and R$_6$, which may be identical or different, are chosen from alkyl groups comprising from 1 to 18 carbon atoms and benzyl groups; and
[X]$^-$ is chosen from methosulphate anions and halides, such as chloride and bromide.

The copolymers of family (1) additionally comprise at least one unit deriving from comonomers which can be chosen from acrylamides, methacrylamides, diacetone acrylamides, acrylamides and methacrylamides substituted on the nitrogen by lower (C$_1$-C$_4$) alkyl groups, groups derived from acrylic and methacrylic acids and from their esters, vinyllactams, such as vinylpyrrolidone and vinylcaprolactam, and vinyl esters.

Thus, examples of copolymers of family (1) include, but are not limited to:
copolymers of acrylamide and of dimethylaminoethyl methacrylate which are quaternized with dimethyl sulphate or with a dimethyl halide, such as that sold under the name Hercofloc® by Hercules,
copolymers of acrylamide and of methacryloyloxyethyltrimethylammonium chloride, described, for example, in European Patent Application No. 0 080 976 and sold under the name Binaquat P 100 by Ciba-Geigy,
copolymers of acrylamide and of methacryloyloxyethyltrimethylammonium methosulphate, such as that sold under the name Reten by Hercules,
vinylpyrrolidone/dialkylaminoalkyl acrylate and methacrylate copolymers, which may or may not be quaternized, such as the products sold under the name "Gafquat®" by ISP, for example, "Gafquat® 734" and "Gafquat® 755", and the products named "Copolymer® 845, 958, and 937". These polymers are described, for example, in French Patent Nos. 2 077 143 and 2 393 573,
dimethylaminoethyl methacrylate/vinylcaprolactam/vinylpyrrolidone terpolymers, such as the product sold under the name Gaffix® VC 713 by ISP, and
vinylpyrrolidone/quaternized dimethylaminopropylmethacrylamide copolymers, such as the product sold under the name "Gafquat® HS 100" by ISP.

(2) Cationic polysaccharides, optionally comprising quaternary ammonium, such as those described in U.S. Pat. Nos. 3,589,578 and 4,031,307, such as guar gums comprising trialkylammonium cationic groups. Such products are sold, for instance, under the trade names Jaguar C13 S, Jaguar C15, and Jaguar C17 by Meyhall.

(3) Quaternary copolymers of vinylpyrrolidone and of vinylimidazole.

(4) Chitosans and their salts; such as chitosan acetate, lactate, glutamate, gluconate, and pyrrolidonecarboxylate.

Non-limiting examples of such compounds include the chitosan having a degree of deacetylation of 90.5% by weight sold under the name Kytan Brut Standard by Aber Technologies and the chitosan pyrrolidonecarboxylate sold under the name Kytamer® PC by Amerchol.

(5) Cationic cellulose derivatives, such as the copolymers of cellulose and of cellulose derivatives grafted with a water-soluble monomer comprising a quaternary ammonium and described, for example, in U.S. Pat. No. 4,131,576, such as hydroxyalkylcelluloses, for example hydroxymethyl-, hydroxyethyl- and hydroxypropylcelluloses, grafted for instance, with a salt chosen from methacryloyloxyethyltrimethylammonium, methacrylamidopropyltrimethylammonium, and dimethyldiallylammonium salts.

Marketed products corresponding to this definition include, for example, the products sold under the names "Celquat L 200" and "Celquat H 100" by National Starch.

The anionic fixing polymers which may be used in accordance with the present disclosure include polymers comprising groups derived from carboxylic, sulphonic, and phosphoric acid and have a number-average molecular weight ranging from 500 to 5,000,000.

The carboxyl groups may be contributed by unsaturated mono- or dicarboxylic acid monomers such as those corresponding to the following formula:

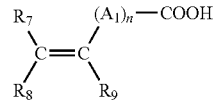

wherein n is an integer ranging from 0 to 10, A$_1$ is a methylene group, optionally connected to the carbon atom of the unsaturated group or to the neighboring methylene group when n is greater than 1 via a heteroatom, such as oxygen and sulphur, R$_7$ is chosen from hydrogen, phenyl groups, and benzyl groups, R$_8$ is chosen from hydrogen, lower alkyl groups, and carboxyl groups, and R$_9$ is chosen from hydrogen, lower alkyl groups, —CH$_2$—COOH groups, phenyl groups, and benzyl groups.

In the above mentioned formula, a lower alkyl group may be chosen, for example, from groups comprising from 1 to 4 carbon atoms, such as methyl and ethyl groups.

Non-limiting examples of anionic fixing polymers comprising carboxyl groups according to the present disclosure include:
A) Homo- and copolymers of acrylic and methacrylic acid and their salts, such as the products sold under the names Versicol® E or K by Allied Colloid and Ultrahold® by BASF, the copolymers of acrylic acid and of acrylamide sold in the form of their sodium salts under the names Reten 421, 423, and 425 by Hercules, and the sodium salts of polyhydroxycarboxylic acids.

B) Copolymers of acrylic and methacrylic acid with a monoethylenic monomer, such as ethylene, styrene, vinyl esters, and esters of acrylic and methacrylic acid, optionally grafted onto a polyalkylene glycol, such as polyethylene glycol, and optionally crosslinked. Such polymers are described, for example, in French Patent No. 1 222 944 and German Patent Application No. 2 330 956, the copolymers of this type comprising, in their chain, an optionally N-alkylated and/or -hydroxyalkylated acrylamide unit, such as those described, for example, in Luxembourgian Patent Applications Nos. 75370 and 75371 and provided under the name Quadramer by American Cyanamid. Methacrylic acid/ethyl acrylate/tert-butyl acrylate terpolymers may also be used, such as the product sold under the name Luvimer® 100 P by BASF, and methacrylic acid/acrylic acid/ethyl acrylate/methyl methacrylate copolymers in aqueous dispersion, such as those sold under the name Amerhold® DR 25 by Amerchol.

C) Copolymers of crotonic acid, such as those comprising, in their chain, at least one unit chosen from vinyl acetate and propionate units and optionally other monomers, such as allyl and methallyl esters, vinyl ethers and vinyl esters of a linear or branched saturated carboxylic acid comprising a long hydrocarbon chain, such as those comprising at least 5 carbon atoms, it optionally being possible for these polymers to be grafted or crosslinked, and vinyl, allyl, and methallyl esters of α- and β-cyclic carboxylic acids. Such polymers are described, for example, in French Patents Nos. 1 222 944, 1 580 545, 2 265 782, 2 265 781, 1 564 110, and 2 439 798. Examples of commercial products falling within this class are the Resins 28-29-30, 26-13-14, and 28-13-10 sold by National Starch.

D) Copolymers of $C_4$-$C_8$ monounsaturated carboxylic acids and anhydrides chosen from:

copolymers comprising (i) at least one monomer chosen from maleic, fumaric, and itaconic acids and anhydrides and (ii) at least one monomer chosen from vinyl esters, vinyl ethers, vinyl halides, phenylvinyl derivatives, and acrylic acid and its esters, the anhydride functional groups of these copolymers optionally being monoesterified or monoamidated. Such polymers are described, for instance, in U.S. Pat. Nos. 2,047,398, 2,723,248, and 2,102,113 and British Patent No. 839 805. Examples of commercial products falling within this definition include those sold under the names Gantrez® AN and ES by ISP;

copolymers comprising (i) at least one monomer chosen from maleic, citraconic, and itaconic anhydride units and (ii) at least one monomer chosen from allyl and methallyl esters, optionally comprising at least one monomer chosen from acrylamide, methacrylamide, α-olefin, acrylic and methacrylic ester, acrylic and methacrylic acid, and vinylpyrrolidone groups in their chain, the anhydride functional groups of these copolymers optionally being monoesterified or monoamidated.

These polymers are described, for example, in French Patents Nos. 2 350 384 and 2 357 241.

E) Polyacrylamides comprising carboxylate groups.

The homopolymers and copolymers comprising sulpho groups include, by way of non-limiting example, polymers comprising at least one unit chosen from vinylsulphonic, styrenesulphonic, naphthalenesulphonic, and acrylamidoalkylsulphonic units.

Examples of these polymers include, but are not limited to:

salts of polyvinylsulphonic acid having a molecular weight ranging from 1,000 to 100,000, as well as copolymers with an unsaturated comonomer, such as acrylic and methacrylic acids and their esters, as well as acrylamide and its derivatives, vinyl ethers, and vinylpyrrolidone;

salts of polystyrenesulphonic acid, such as the sodium salts sold, for example, under the names Flexan® 500 and Flexan® 130 by National Starch. These compounds are described, for example, in French Patent No. 2 198 719; and salts of polyacrylamidosulphonic acids, such as those mentioned in U.S. Pat. No. 4,128,631, for example, the polyacrylamidoethylpropanesulphonic acid sold under the name Cosmedia Polymer HSP 1180 by Henkel.

In at least one embodiment, the anionic fixing polymers are chosen from acrylic acid copolymers, such as the acrylic acid/ethyl acrylate/N-tert-butylacrylamide terpolymers sold, for example, under the name Ultrahold® Strong by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold, for instance, under the name Resin 28-29-30 by National Starch, polymers derived from maleic, fumaric, and itaconic acids and anhydrides with vinyl esters, vinyl ethers, vinyl halides, phenylvinyl derivatives, and acrylic acid and its esters, such as the monoesterified methyl vinyl ether/maleic anhydride copolymers sold, for example, under the name Gantrez® by ISP, the copolymers of methacrylic acid and of methyl methacrylate sold under the name Eudragit® L by Rohm Pharma, the copolymers of methacrylic acid and of ethyl acrylate sold under the names Luvimer® MAEX and MAE by BASF, the vinyl acetate/crotonic acid copolymers sold, for instance, under the name Luviset CA 66 by BASF, and the vinyl acetate/crotonic acid copolymers grafted by polyethylene glycol sold, for instance, under the name Aristoflex® A by BASF.

According to another embodiment, the anionic fixing polymers are chosen from the monoesterified methyl vinyl ether/maleic anhydride copolymers sold under the name Gantrez® ES 425 by ISP, the acrylic acid/ethyl acrylate/N-tert-butylacrylamide terpolymers sold under the name Ultrahold® Strong by BASF, the copolymers of methacrylic acid and of methyl methacrylate sold under the name Eudragit® L by Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by National Starch, and the copolymers of methacrylic acid and of ethyl acrylate sold under the names Luvimer® MAEX and MAE by BASF.

The amphoteric fixing polymers which can be used in accordance with the present disclosure may be chosen, by way of non-limiting example, from polymers comprising B and C units distributed randomly in the polymer chain, wherein B is a unit deriving from a monomer comprising at least one basic nitrogen atom and C is a unit deriving from an acidic monomer comprising at least one group chosen from carboxyl and sulpho groups, or else B and C are groups deriving from zwitterionic carboxybetaine and sulphobetaine monomers;

B and C may also be cationic polymer chains comprising primary, secondary, tertiary, and/or quaternary amine groups, in which at least one of the amine groups carries a group chosen from carboxyl and sulpho groups connected via a hydrocarbon group, or else B and C may form part of a chain of a polymer comprising an α,β-dicarboxyethylene unit, one of the carboxyl groups of which has been reacted with a polyamine comprising at least one group chosen from primary and secondary amine groups.

In at least one embodiment, the amphoteric fixing polymers corresponding to the definition given above are chosen from:

1) Copolymers comprising acidic vinyl units and comprising basic vinyl units, such as those resulting from the copolymerization of a monomer derived from a vinyl compound carrying a carboxyl group, such as acrylic acid, methacrylic acid, maleic acid, and α-chloroacrylic acid, and of a basic monomer derived from a substituted vinyl compound comprising at least one basic atom, such as dialkylaminoalkyl methacrylate and acrylate and dialkylaminoalkylmethacrylamide and -acrylamide. Such compounds are described, for instance, in U.S. Pat. No. 3,836,537.

2) Polymers comprising units deriving:

a) from at least one monomer chosen from acrylamides and methacrylamides substituted on the nitrogen atom by an alkyl group, b) from at least one acidic comonomer comprising at least one reactive carboxyl group, and c) from at least one basic comonomer, such as esters comprising primary, secondary, tertiary, and quaternary amine substituents of acrylic and methacrylic acids and the quaternization product of dimethylaminoethyl methacrylate with dimethyl or diethyl sulphate.

According to one embodiment, the N-substituted acrylamides and methacrylamides may be chosen from compounds in which the alkyl groups comprise from 2 to 12 carbon atoms, such as N-ethylacrylamide, N-tert-butylacrylamide, N-tert-octylacrylamide, N-octylacrylamide, N-decylacrylamide, and N-dodecylacrylamide, and the corresponding methacrylamides.

The acidic comonomers may be chosen, by way of non-limiting example, from acrylic, methacrylic, crotonic, itaconic, maleic, and fumaric acids and alkyl monoesters comprising from 1 to 4 carbon atoms of maleic and fumaric acids and anhydrides.

The basic comonomers may be chosen, by way of non-limiting example, from aminoethyl, butylaminoethyl, N,N'-dimethylaminoethyl, and N-tert-butylaminoethyl methacrylates.

The copolymers for which the CTFA name (4th Ed., 1991) is Octylacrylamide/acrylates/butylaminoethyl methacrylate copolymer, such as the products sold under the name Amphomer® and Lovocryl® 47 by National Starch may be used in accordance with the present disclosure.

3) Partially or completely acylated and crosslinked polyaminoamides deriving from polyaminoamides of formula (XVII):

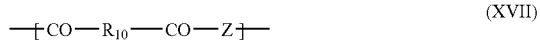

(XVII)

wherein $R_{10}$ is a divalent group derived from a group chosen from saturated dicarboxylic acids, aliphatic mono- and dicarboxylic acids comprising an ethylenic double bond, esters of a lower alkanol comprising from 1 to 6 carbon atoms of these acids, and groups deriving from the addition of any one of the said acids with a bisprimary or bissecondary amine, and Z is a group deriving from a bisprimary, mono-, or bissecondary polyalkylenepolyamine, and in at least one embodiment, comprises:

a) in an amount ranging from 60 to 100 mol %, the group:

(XVIII)

wherein x=2 and p=2 or 3, or else x=3 and p=2;

this group deriving from diethylenetriamine, triethylenetetraamine, or dipropylenetriamine;

b) in an amount ranging from 0 to 40 mol %, the above group (XVIII), in which x=2 and p=1 and which derives from ethylenediamine, or the group deriving from piperazine:

c) in an amount ranging from 0 to 20 mol %, the group —NH—$(CH_2)_6$—NH-deriving from hexamethylenediamine, these polyaminoamides being crosslinked by addition reaction of a bifunctional crosslinking agent chosen from epihalohydrins, diepoxides, dianhydrides, and bisunsaturated derivatives, via 0.025 to 0.35 mol of crosslinking agent per amine group of the polyaminoamide, and acylated by reaction with an agent chosen from acrylic acid, chloroacetic acid, alkanesultones and their salts.

The saturated carboxylic acids may be chosen, by way of non-limiting example, from acids comprising from 6 to 10 carbon atoms, such as adipic, 2,2,4-trimethyladipic, 2,4,4-trimethyladipic, and terephthalic acids, and the acids comprising an ethylenic double bond, for example, acrylic, methacrylic, and itaconic acids.

The alkanesultones used in the acylation may be chosen from propane- and butanesultone and the salts of the acylating agents may be chosen from the sodium or potassium salts.

4) Polymers comprising zwitterionic units of formula:

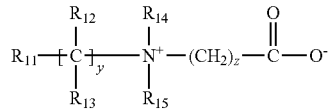

wherein $R_{11}$ is a polymerizable unsaturated group, such as acrylate, methacrylate, acrylamide, and methacrylamide groups, y and z, which may be identical or different, are integers from 1 to 3, $R_{12}$ and $R_{13}$, which may be identical or different, are chosen from hydrogen and methyl, ethyl, and propyl groups, and $R_{14}$ and $R_{15}$, which may be identical or different, are chosen from hydrogen and alkyl groups such that the sum of the carbon atoms in $R_{14}$ and $R_{15}$ is less than or equal to 10.

The polymers comprising such units may also comprise units derived from non-zwitterionic monomers, such as dimethyl- and diethylaminoethyl acrylate and methacrylate and alkyl acrylates and methacrylates, acrylamides, and methacrylamides, and vinyl acetate.

Mention may be made, by way of non-limiting example, of methyl methacrylate/dimethylcarboxymethylammonioethylmethyl methacrylate copolymers, such as the product sold under the name Diaformer Z301 by Sandoz.

5) Polymers derived from chitosan comprising monomer units corresponding to the following formulae:

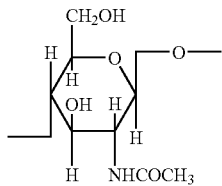
(D)

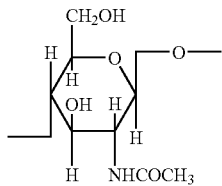
(E)

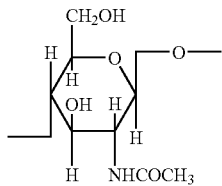
(F)

the unit (D) being present in an amount ranging from 0 to 30%, the unit (E) in an amount ranging from 5 to 50%, and the unit (F) in an amount ranging from 30 to 90%, it being understood that, in this unit (F), $R_{16}$ is a group of formula:

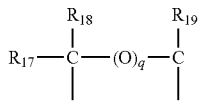

wherein if q=0, $R_{17}$, $R_{18}$, and $R_{19}$, which may be identical or different, are chosen from hydrogen, methyl, hydroxyl, acetoxy, and amino residues, monoalkylamino residues, and dialkylamino residues, optionally interrupted by at least one nitrogen atom and/or optionally substituted by at least one group chosen from amino, hydroxyl, carboxyl, alkylthio, and sulpho groups, and alkylthio residues in which the alkyl group carries an amino residue, at least one of the $R_{17}$, $R_{18}$, and $R_{19}$ groups being, in this case, a hydrogen atom;

or, if q=1, $R_{17}$, $R_{18}$, and $R^{19}$ are each hydrogen, and the acid and base addition salts of these compounds.

6) Polymers comprising units chosen from those of formula (XIX) which are, for example, described in French Patent No. 1 400 366:

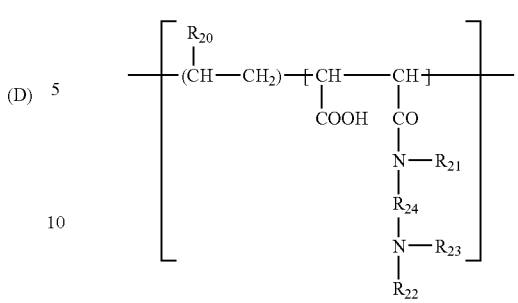
(XIX)

wherein $R_{20}$ is chosen from hydrogen, $CH_3O$, $CH_3CH_2O$, and phenyl groups, $R_{21}$ is chosen from hydrogen and lower alkyl groups, such as methyl and ethyl, $R_{22}$ is chosen from hydrogen and lower $C_1$-$C_6$ alkyl groups, such as methyl and ethyl, and $R_{23}$ is chosen from lower $C_1$-$C_6$ alkyl groups, such as methyl and ethyl, and groups chosen from those of formula: —$R_{24}$—N($R_{22}$)$_2$, wherein $R_{24}$ is chosen from —$CH_2$—$CH_2$—, —$CH_2$—$CH_2$—$CH_2$—, and —$CH_2$—$CH$($CH_3$)— groups and $R_{22}$ is as defined above.

7) Polymers derived from the N-carboxyalkylation of chitosan, such as the N-(carboxymethyl)chitosan and the N-(carboxybutyl)chitosan sold under the name "Evalsan" by Jan Dekker.

8) Amphoteric polymers of the -D-X-D-X- type chosen from:
a) polymers obtained by reaction of chloroacetic acid or sodium chloroacetate with compounds comprising at least one unit of formula (XX):

-D-X-D-X-D-  (XX)

where D is a group

and X is chosen from the symbols E and E', wherein E and E', which may be identical or different, are chosen from bivalent groups which are straight- or branched-chain alkylene groups comprising up to 7 carbon atoms in the main chain which may be unsubstituted or substituted by hydroxyl groups and which may additionally comprise at least one atom chosen from oxygen, nitrogen, and sulphur atoms and 1 to 3 aromatic and/or heterocyclic rings; the oxygen, nitrogen, and sulphur atoms being present in the form of ether, thioether, sulphoxide, sulphone, sulphonium, alkylamine, and/or alkenylamine, hydroxyl, benzylamine, amine oxide, quaternary ammonium, amide, imide, alcohol, ester, and/or urethane groups.

b) polymers of formula (XXI'):

-D-X-D-X-  (XXI')

where D is a group

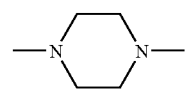

and X is chosen from the symbols E and E', and at least once E', E having the meaning indicated above and E' being chosen from bivalent groups which are straight- or branched-chain alkylene groups comprising up to 7 carbon atoms in the main chain which may be unsubstituted or substituted by at least onehydroxyl group and which comprises at least one nitrogen atom, the nitrogen atom being substituted by an alkyl chain optionally interrupted by an oxygen atom and comprising at least one carboxyl functional group and at least one hydroxyl functional group and betainized by reaction with chloroacetic acid or sodium chloroacetate.

9) ($C_1$-$C_5$)Alkyl vinyl ether/maleic anhydride copolymers partially modified by semiamidation with an N,N-dialkylaminoalkylamine, such as N,N-dimethylaminopropylamine, or by semiesterification with an N,N-dialkylaminoalkanol. These copolymers may also comprise other vinyl comonomers, such as vinylcaprolactam.

According to at least one embodiment, the amphoteric fixing polymers may be chosen from those of family 3), such as the copolymers with the CTFA name of Octylacrylamide/acrylates/butylaminoethyl methacrylate copolymer, such as the products sold under the names Amphomer®, Amphomer® LV 71, and Lovocryl® 47 by National Starch, and those of family 4), such as methyl methacrylate/dimethylcarboxymethyl-ammonioethylmethyl methacrylate copolymers, sold, for example, under the name Diaformer® Z301 by Sandoz.

The non-ionic fixing polymers which can be used according to the present disclosure may be chosen, by way of non-limiting example, from:

polyalkyloxazolines;

vinyl acetate homopolymers;

vinyl acetate copolymers, for example copolymers of vinyl acetate and of acrylic ester, copolymers of vinyl acetate and of ethylene, and copolymers of vinyl acetate and of maleic ester, for example, of dibutyl maleate;

acrylic ester homopolymers and copolymers, for example, copolymers of alkyl acrylates and of alkyl methacrylates, such as the products provided by Rohm & Haas under the names Primal® AC-261 K and Eudragit® NE 30 D, by BASF under the name 8845 and by Hoechst under the name Appretan® N9212;

copolymers of acrylonitrile and of a non-ionic monomer chosen, for example, from butadiene and alkyl (meth)acrylates; for instance, the products provided under the name CJ 0601 B by Rohm & Haas;

styrene homopolymers;

styrene copolymers, for example, copolymers of styrene and of alkyl (meth)acrylate, such as the products Mowilith® LDM 6911, Mowilith® DM 611, and Mowilith® LDM 6070 provided by Hoechst and the products Rhodopas® SD 215 and Rhodopas® DS 910 provided by Rhodia Chimie, copolymers of styrene, of alkyl methacrylate and of alkyl acrylate, copolymers of styrene and of butadiene or copolymers of styrene, of butadiene and of vinylpyridine;

polyamides;

vinyllactam homopolymers other than vinylpyrrolidone homopolymers, such as the polyvinylcaprolactam sold under the name Luviskol® Plus by BASF; and vinyllactam copolymers, such as a poly(vinylpyrrolidone/vinyllactam) copolymer sold under the trade name Luvitec® VPC 55K65W by BASF, poly(vinylpyrrolidone/vinyl acetate) copolymers, such as those sold under the name PVPVA® S630L by ISP and Luviskol® VA 73, VA 64, VA 55, VA 37, and VA 28 by BASF, and poly(vinylpyrrolidone/vinyl acetate/vinyl propionate) terpolymers, for example, that sold under the name Luviskol® VAP 343 by BASF.

The alkyl groups of the non-ionic polymers mentioned above may comprise, in at least one embodiment, from 1 to 6 carbon atoms.

The at least one fixing polymer may also be chosen from cationic, non-ionic, anionic, and amphoteric polyurethanes which may or may not be functionalized and which may or may not be silicone-comprising, and mixtures thereof.

The polyurethanes may be chosen, for instance, from those described in European Patent Application Nos. 0 751 162, 0 637 600, 0 648 485, 0 656 021, and 0 619 111, French Patent Application No. 2 743 297, and International Patent Application Publication No. WO 94/03510.

Non-limiting examples of polyurethanes suitable in accordance with the present disclosure include the products sold under the names Luviset PURE and Luviset® Si PUR by BASF.

The at least one additional fixing polymer may be present in the cosmetic composition according to the present disclosure in an amount ranging from 0.01 to 20% by weight, for example, from 0.05 to 15% by weight, or from 0.1 to 10% by weight, with respect to the total weight of the cosmetic composition.

The composition according to the present disclosure may further comprise at least one surfactant, which may be ionic or non-ionic.

The at least one ionic surfactant used in the cosmetic composition may be chosen from cationic surfactants.

Non-limiting examples of cationic surfactants which can be used in the cosmetic composition include salts of primary, secondary, and tertiary fatty amines which are optionally polyoxyalkylenated, quaternary ammonium salts, and mixtures thereof.

Examples of quaternary ammonium salts include, but are not limited to:

quaternary ammonium salts of formula (I):

wherein:

$R_8$ to $R_{11}$, which may be identical or different, are chosen from linear and branched aliphatic radicals comprising from 1 to 30 carbon atoms and aromatic radicals, such as aryl and alkylaryl. The aliphatic radicals may optionally comprise at least one heteroatom, for example, oxygen, nitrogen, sulphur, and halogens.

The aliphatic radicals may be chosen, by way of non-limiting example, from alkyl radicals, alkoxy radicals, polyoxy($C_2$-$C_6$)alkylene radicals, alkylamido radicals, ($C_{12}$-$C_{22}$) alkylamido($C_2$-$C_6$) alkyl radicals, ($C_{12}$-$C_{22}$)alkyl acetate radicals and hydroxyalkyl radical comprising from 1 to 30 carbon atoms; and $X^-$ is an anion chosen from halides, phosphates, acetates, lactates, ($C_2$-$C_6$)alkyl sulphates, alkylsulphonates, and alkylarylsulphonates;

imidazoline quaternary ammonium salts, for example, those of formula (II):

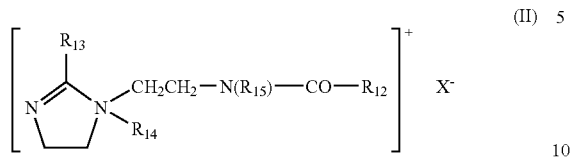

wherein $R_{12}$ is chosen from alkenyl and alkyl radicals comprising from 8 to 30 carbon atoms, for example, derivatives of tallow fatty acids, $R_{13}$ is chosen from hydrogen, $C_1$-$C_4$ alkyl radicals and alkenyl and alkyl radicals comprising from 8 to 30 carbon atoms, $R_{14}$ is chosen from $C_1$-$C_4$ alkyl radicals, $R_{15}$ is chosen from hydrogen and $C_1$-$C_4$ alkyl radicals, and $X^-$ is an anion chosen from halides, phosphates, acetates, lactates, alkyl sulphates, alkylsulphonates, and alkylarylsulphonates. In at least one embodiment, $R_{12}$ and $R^{13}$ are chosen from mixtures of alkenyl and alkyl radicals comprising from 12 to 21 carbon atoms, for example, derivatives of tallow fatty acids, $R_{14}$ is a methyl radical, and $R_{15}$ is a hydrogen atom. Such a product is, for example, sold under the name Rewoquat® W 75 by Rewo;

di(quaternary ammonium) salts of formula (III):

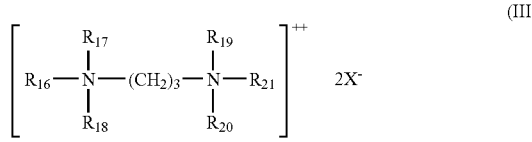

wherein $R_{16}$ is an aliphatic radical comprising approximately from 16 to 30 carbon atoms, $R_{17}$, $R_{18}$, $R_{19}$, $R_{20}$, and $R_{21}$, which may be identical or different, are chosen from hydrogen and alkyl radicals comprising from 1 to 4 carbon atoms, and $X^-$ is an anion chosen from halides, acetates, phosphates, nitrates, and methyl sulphates. Such di(quaternary ammonium) salts include, for example, propanetallowdiammonium dichloride;

quaternary ammonium salts comprising at least one ester functional group, such as those of formula (IV):

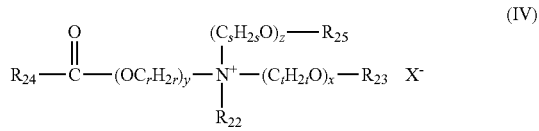

wherein:

$R_{22}$ is chosen from $C_1$-$C_6$ alkyl radicals and $C_1$-$C_6$ hydroxyalkyl and dihydroxyalkyl radicals;

$R_{23}$ is chosen from hydrogen, saturated and unsaturated, linear and branched, $C_1$-$C_{22}$ hydrocarbon radicals, $R_{27}$, and

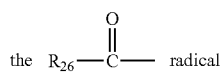

the $R_{26}$—C— radical $R_{25}$ is chosen from hydrogen, saturated and unsaturated, linear and branched, $C_1$-$C_6$ hydrocarbon radicals, $R_{29}$, and:

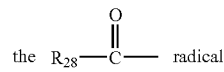

the $R_{28}$—C— radical $R_{24}$, $R_{26}$, and $R_{28}$, which may be identical or different, are chosen from saturated and unsaturated, linear and branched, $C_7$-$C_2$, hydrocarbon radicals;

r, s, and t, which may be identical or different, are integers ranging from 2 to 6;

y is an integer ranging from 1 to 10;

x and z, which may be identical or different, are integers ranging from 0 to 10;

$X^-$ is an organic or inorganic, simple or complex anion;

with the proviso that the sum x+y+z has a value ranging from 1 to 15, that, when x has the value 0, then $R_{23}$ denotes $R_{27}$ and that, when z has the value 0, then $R_{25}$ denotes $R_{29}$.

The $R_{22}$ alkyl radicals may be linear or branched and, in at least one embodiment, linear.

In another embodiment, $R_{22}$ is chosen from methyl, ethyl, hydroxyethyl, and dihydroxypropyl radicals, and, in a further embodiment, it is chosen from methyl and ethyl radicals.

According to yet another embodiment, the sum x+y+z has a value ranging from 1 to 10.

When $R_{23}$ is an $R_{27}$ hydrocarbon radical, it can be long and can comprise from 12 to 22 carbon atoms, or it can be short and can comprise from 1 to 3 carbon atoms.

When $R_{25}$ is an $R_{29}$ hydrocarbon radical, it may comprise from 1 to 3 carbon atoms.

In at least one embodiment, $R_{24}$, $R_{26}$, and $R_{28}$, which may be identical or different, are chosen from saturated and unsaturated, linear and branched, $C_{11}$-$C_{21}$ hydrocarbon radicals, for example, saturated and unsaturated, linear and branched, $C_{11}$-$C_{21}$ alkyl and alkenyl radicals.

In another embodiment, x and z, which may be identical or different, are equal to 0 or 1.

According to a further embodiment, y is equal to 1.

In yet another embodiment, r, s, and t, which may be identical or different, are equal to 2 or 3, and, in still a further embodiment, they are equal to 2.

According to one embodiment, the anion is chosen from halides (e.g., chloride, bromide, and iodide) and alkyl sulphates, such as methyl sulphate. However, the anion may also be chosen, for example, from methanesulphonate, phosphate, nitrate, tosylate, anions derived from an organic acid, such as acetate and lactate, and any other anion compatible with the ammonium comprising an ester functional group.

In another embodiment, the anion $X^-$ is chosen from chloride and methyl sulphate.

According to a further embodiment, the ammonium salts may be chosen from those of formula (IV) in which:

$R_{22}$ is chosen from methyl and ethyl radicals, x and y are equal to 1;

z is equal to 0 or 1;

r, s, and t are equal to 2;

$R_{23}$ is chosen from hydrogen, methyl, ethyl, and $C_{14}$-$C_{22}$ hydrocarbon radicals, and the 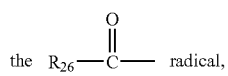 radical, $R_{25}$ is chosen from hydrogen and the 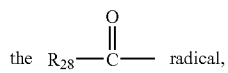 radical, $R_{24}$, $R_{26}$, and $R_{28}$, which may be identical or different, are chosen from saturated and unsaturated, linear and branched, $C_{13}$-$C_{17}$ hydrocarbon radicals, for example, saturated and unsaturated, linear and branched, $C_{13}$-$C_{17}$ alkyl and alkenyl radicals.

In yet another embodiment, the hydrocarbon radicals are linear.

Non-limiting examples of compounds of formula (IV) include diacyloxyethyldimethylammonium, diacyloxyethyl(hydroxyethyl)methyl-ammonium, monoacyloxyethyl(dihydroxyethyl)methylammonium, triacyloxy-ethyl(methyl)ammonium, and monoacyloxyethyl(hydroxyethyl)dimethylammonium salts (e.g., chloride and methyl sulphate) and mixtures thereof. The acyl radicals may comprise from 14 to 18 carbon atoms and may, in at least one embodiment, originate from a vegetable oil, such as palm oil and sunflower oil. When the compound comprises several acyl radicals, the latter can be identical or different.

These products may be obtained, for example, by direct esterification of triethanolamine, of triisopropanolamine, of alkyldiethanolamine or of alkyldiisopropanolamine, which may be optionally oxyalkylenated, with fatty acids or with mixtures of fatty acids of vegetable or animal origin or by transesterification of their methyl esters. This esterification is followed by a quaternization using an alkylating agent, such as alkyl (e.g., methyl and ethyl) halides, dialkyl (e.g., methyl and ethyl) sulphates, methyl methanesulphonate, methyl para-toluenesulphonate, and glycol and glycerol chlorohydrin.

Such compounds are, for example, sold under the names Dehyquart® by Henkel, Stepanquat® by Stepan, Noxamium® by Ceca, and Rewoquat® WE 18 by Rewo-Witco.

According to at least one embodiment, the composition according to the present disclosure comprises a mixture of quaternary ammonium mono-, di-, and triester salts, with a majority by weight of diester salts.

A suitable mixture of ammonium salts may include, by way of non-limiting example, a mixture comprising 15 to 30% by weight of acyloxyethyl(dihydroxyethyl)methyl-ammonium methyl sulphate, 45 to 60% of diacyloxyethyl(hydroxyethyl)methyl-ammonium methyl sulphate, and 15 to 30% of triacyloxyethyl(methyl)ammonium methyl sulphate, the acyl radicals comprising from 14 to 18 carbon atoms and originating from optionally partially hydrogenated palm oil.

It is also possible to use ammonium salts comprising at least one ester functional group described, for instance, in U.S. Pat. Nos. 4,874,554 and 4,137,180.

In at least one embodiment, the quaternary ammonium salts of formula (I) may be chosen from tetraalkylammonium chlorides, for example, dialkyldimethylammonium and alkyltrimethylammonium chlorides, in which the alkyl radical comprises from 12 to 22 carbon atoms, such as behenyltrimethylammonium, distearyidimethylammonium, cetyl-trimethylammonium, and benzyldimethylstearylammonium chlorides; and palmitylamidopropyltrimethylammonium chloride and stearamidopropyldimethyl(myristyl acetate) ammonium chloride, sold under the name Ceraphyl® 70 by Van Dyk.

According to another embodiment, the cationic surfactants are chosen from quaternary ammonium salts, such as cetyltrimethylammonium chloride, behenyltrimethylammonium chloride, and palmitylamidopropyltrimethylammonium chloride.

The at least one ionic surfactant which can be used in the cosmetic composition can also be chosen from anionic surfactants.

Non-limiting examples of anionic surfactants which can be used in the cosmetic composition according to the present disclosure include the salts, for example, the alkali metal salts, such as the sodium salts, the ammonium salts, the amine salts, the aminoalcohol salts, and the alkaline earth metal salts, for example, magnesium salts, of: alkyl sulphates, alkyl ether sulphates, alkylamido ether sulphates, alkylaryl polyether sulphates, monoglyceride sulphates; alkylsulphonates, alkylamide sulphonates, alkylaryl sulphonates, α-olefinsulphonates, paraffinsulphonates, alkyl sulphosuccinates, alkyl ether sulphosuccinates, alkylamidesulphosuccinates, alkyl sulphoacetates, acylsarcosinates, and acylglutamates, the alkyl and acyl groups of all these compounds comprising from 6 to 24 carbon atoms and the aryl group being chosen from phenyl and benzyl groups.

The anionic surfactants may also be chosen from $C_6$-$C_{24}$ monoalkyl esters of polyglycosidedicarboxylic acids, such as alkyl glucosidecitrates, alkyl polyglycosidetartrates, and alkyl polyglycosidesulphosuccinates, alkyl sulphosuccinamates, acylisethionates, and N-acyltaurates, the alkyl or acyl group of all these compounds comprising from 12 to 20 carbon atoms.

Other non-limiting examples of suitable anionic surfactants include acyllactylates, the acyl group of which comprises from 8 to 20 carbon atoms.

Further examples of anionic surfactants include, but are not limited to, alkyl-D-galactosideuronic acids and their salts, polyoxyalkylenated ($C_6$-$C_{24}$)alkyl ether carboxylic acids and their salts, polyoxyalkylenated ($C_6$-$C_{24}$)alkyl($C_6$-$C_{24}$)aryl ether carboxylic acids and their salts, polyoxyalkylenated ($C_6$-$C_{24}$)alkylamido ether carboxylic acids and their salts, for instance, those comprising from 2 to 50 ethylene oxide units, and mixtures thereof.

According to one embodiment, the anionic surfactants are chosen from alkyl sulphates, alkyl ether sulphates, and alkyl ether carboxylates, and mixtures thereof, in the form of alkali metal, alkaline earth metal, ammonium, amine, and aminoalcohol salts.

In another embodiment, the at least one ionic surfactant is chosen from cationic surfactants.

The at least one non-ionic surfactant which can be used in the cosmetic composition of the present disclosure may be chosen from compounds known in the art (see, for example, the "Handbook of Surfactants" by M. R. Porter, published by Blackie & Son (Glasgow and London), 1991, pp 116-178). They may be chosen, by way of non-limiting example, from alcohols, α-diols, ($C_1$-$C_{20}$)alkylphenols, and polyethoxylated, polypropoxylated, and polyglycerolated fatty acids having a fatty chain comprising, for example, from 8 to 18 carbon atoms, it being possible for the number of ethylene oxide or propylene oxide groups to range, for example, from 2 to 50 and it being possible for the number of glycerol groups to range, for example, from 2 to 30.

Further non-limiting examples of non-ionic surfactants include condensates of ethylene oxide and of propylene oxide with fatty alcohols; polyethoxylated fatty amides comprising from 2 to 30 ethylene oxide units, polyglycerolated fatty amides comprising on average from 1 to 5 glycerol groups, for instance, from 1.5 to 4, sorbitan ethoxylated fatty acid esters comprising from 2 to 30 ethylene oxide units, sucrose fatty acid esters, polyethylene glycol esters of fatty acids, (($C_6$-$C_{24}$)alkyl)polyglycosides, N—(($C_6$-$C_{24}$)alkyl)glucamine derivatives and amine oxides, such as oxides of (($C_{10}$-$C_{14}$)alkyl)amines and N—(($C_{10}$-$C_{14}$)acyl)aminopropylmorpholine oxides.

According to one embodiment, the at least one non-ionic surfactant may be chosen from polyethoxylated, polypropoxylated, and polyglycerolated alcohols.

The at least one surfactant may be present in the composition in an amount ranging from 0.01 to 20% by weight, for example, from 0.05 to 10% by weight, or from 0.1 to 5% by weight, with respect to the total weight of the composition.

The cosmetic composition according to the present disclosure may optionally further comprise at least one cosmetic adjuvant chosen from conditioning agents of ester type, antimousseing agents, moisturizing agents, emollients, glycols, plasticizers, inorganic thickening agents, polymeric and non-polymeric and associative and non-associative organic thickening agents, water-soluble and fat-soluble sunscreens which may or may not be of silicone nature, permanent and temporary colorings, fragrances, peptizing agents, preservatives, ceramides and pseudoceramides, vitamins and provitamins, including panthenol, proteins, sequestering agents, solubilizing agents, basifying agents, acidifying agents, corrosion inhibitors, reducing agents and antioxidants, oxidizing agents, inorganic fillers, and glitter.

It is to be understood that a person skilled in the art will take care to choose the at least one adjuvant and the amount thereof so as to not harm the properties of the compositions of the present disclosure.

The at least one cosmetic adjuvant may be present in the composition in an amount ranging from 0.001 to 50% by weight, with respect to the total weight of the composition.

As used herein, the term "cosmetically acceptable medium" is understood to mean a medium compatible with keratinous substances such as the hair.

The cosmetically acceptable medium can be chosen from alcoholic, aqueous, and aqueous/alcoholic medium. Thus, the medium can be chosen from water, monoalcohols, and mixtures of water and of at least one cosmetically acceptable monoalcohol, such as lower $C_1$-$C_4$ alcohols, polyol ethers exhibiting a free hydroxyl, and mixtures thereof. In at least one embodiment, the alcohol is ethanol.

Also disclosed herein is a method for the cosmetic treatment of the hair, for example for styling and/or fixing, comprising applying an effective amount of a composition described herein to dry or wet hair and optionally rinsing the hair, after an optional setting time or after an optional drying.

In at least one embodiment, the composition is a leave-in composition.

The present disclosure also relates to the use of a cosmetic composition for fixing fibers.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

The following compositions according to the present disclosure were prepared:

Styling Mousses

| Ingredients | 1 | 2 |
|---|---|---|
| Lambda-Carrageenan (Welgeenan ED 1039, Eurogum) | 1% | 1.2% |
| APG (PLANTACARE® 2000 UP, Cognis) | 5% | — |
| Ionic or non-ionic surfactant (Polysorbate-20) | — | 0.8% |
| Non-ionic fixing polymer (PVP) | — | 3% |
| Ethanol | — | 5% |
| Preservatives, neutralizing agent, fragrance | q.s. | q.s. |
| Water | q.s. for 100 | q.s. for 100 |
| Propellant gas: $CO_2$ | 3.5% | 3.5% |

These compositions, incorporated in an aerosol device, resulted in the formation of a creamy mousse which was easy to spread and which was not expanded to any great extent.

What is claimed is:

1. A cosmetic aerosol composition for the treatment of keratinous fibers, comprising, in a cosmetically acceptable medium,
   at least one lambda-carrageenan polysaccharide,
   at least one ceramide, and
   carbon dioxide as propellant,
packaged in an aerosol device;
   wherein the propellant is present in the cosmetic aerosol composition in an amount ranging from 2 to 3.5% by weight relative to the total weight of the cosmetic aerosol composition, and
   wherein the at least one lambda-carrageenan polysaccharide is present in the cosmetic aerosol composition in an amount ranging from 0.5 to 15% by weight relative to the total weight of the cosmetic aerosol composition.

2. The cosmetic aerosol composition of claim 1, wherein the molecular weight (MW) of the at least one lambda-carrageenan polysaccharide ranges from 100,000 to 1,000,000.

3. The cosmetic aerosol composition of claim 2, wherein the molecular weight (MW) of the at least one lambda-carrageenan polysaccharide ranges from 250,000 to 800,000.

4. The cosmetic aerosol composition of claim 1, wherein the aerosol device can obtain a dry matter throughput (DMT) of greater than or equal to 20 mg/s.

5. The cosmetic aerosol composition of claim 4, wherein the aerosol device can obtain a dry matter throughput (DMT) ranging from 20 to 60 mg/s.

6. The cosmetic aerosol composition of claim 1, wherein a concentration of dry matter (CDM) ranges from 2.5 to 15% by weight relative to the total weight of the cosmetic aerosol composition.

7. The cosmetic aerosol composition of claim 6, wherein the concentration of dry matter ranges from 3.5 to 10% by weight relative to the total weight of the cosmetic aerosol composition.

8. The cosmetic aerosol composition of claim 1, wherein the aerosol composition throughput (ACT) ranges from 500 to 800 mg/s.

9. The cosmetic aerosol composition of claim 8, wherein the aerosol composition throughput (ACT) is equal to about 600 mg/s.

10. The cosmetic aerosol composition of claim 1, wherein the polysaccharide/propellant ratio by weight is greater than 1.

11. The cosmetic aerosol composition of claim 10, wherein the polysaccharide/propellant ratio by weight ranges from 1.2 to 3.

12. The cosmetic aerosol composition of claim 1, further comprising at least one additive chosen from silicones, fatty substances other than ceramides, fixing polymers, and surfactants.

13. The cosmetic aerosol composition of claim 1, wherein the cosmetically acceptable medium is chosen from aqueous, alcoholic, and aqueous/alcoholic mediums.

14. A cosmetic treatment method for styling and/or fixing and/or caring for keratinous fibers comprising applying to the keratinous fibers at least one cosmetic aerosol composition comprising, in a cosmetically acceptable medium,
at least one lambda-carrageenan polysaccharide,
at least one ceramide, and
carbon dioxide as propellant,
packaged in an aerosol device;
wherein the propellant is present in the cosmetic aerosol composition in an amount ranging from 2 to 3.5% by weight relative to the total weight of the cosmetic aerosol composition, and
wherein the at least one lambda-carrageenan polysaccharide is present in the cosmetic aerosol composition in an amount ranging from 0.5 to 15% by weight relative to the total weight of the cosmetic aerosol composition.

15. The cosmetic treatment method of claim 14, wherein the application of the cosmetic aerosol composition is not followed by rinsing.

16. A cosmetic aerosol product for styling and/or fixing and/or caring for keratinous fibers comprising
an aerosol device comprising at least one cosmetic aerosol composition comprising, in a cosmetically acceptable medium,
at least one lambda-carrageenan polysaccharide,
at least one ceramide, and
carbon dioxide as propellant;
wherein the propellant is present in the cosmetic aerosol composition in an amount ranging from 2 to 3.5% by weight relative to the total weight of the cosmetic aerosol composition, and
wherein the at least one lambda-carrageenan polysaccharide is present in the cosmetic aerosol composition in an amount ranging from 0.5 to 15% by weight relative to the total weight of the cosmetic aerosol composition.

* * * * *